United States Patent [19]

Kawaguchi et al.

[11] Patent Number: 5,419,320
[45] Date of Patent: May 30, 1995

[54] METHOD AND APPARATUS FOR OBTAINING AN IMAGE INDICATING METABOLISM IN A BODY

[75] Inventors: Fumio Kawaguchi, Tokyo; Hiroshi Takeuchi, Matsudo; Minoru Yoshida; Takeshi Tajima, both of Tokyo; Kensuke Sekihara, Musashimurayama, all of Japan

[73] Assignee: Hitachi, Ltd., Tokyo, Japan

[21] Appl. No.: 139,086

[22] Filed: Oct. 21, 1993

Related U.S. Application Data

[63] Continuation of Ser. No. 783,216, Oct. 28, 1991, abandoned.

[30] Foreign Application Priority Data

Oct. 26, 1990 [JP] Japan .................................. 2-286997

[51] Int. Cl.⁶ .......................... A61B 6/03; A61B 5/055
[52] U.S. Cl. .................................. 128/633; 128/653.1; 128/653.2; 250/341.1; 378/4; 378/63; 364/413.19
[58] Field of Search ................. 128/633, 653.1, 653.2, 128/660.07; 378/4, 20, 63; 364/413.13, 413.14, 413.19; 250/341

[56] References Cited

U.S. PATENT DOCUMENTS

| | | | |
|---|---|---|---|
| 4,281,645 | 8/1981 | Jöbsis | 128/633 |
| 5,038,786 | 8/1991 | Kojima | 128/653.2 |
| 5,081,992 | 1/1992 | Levin et al. | 128/653.2 |
| 5,148,022 | 9/1992 | Kawaguchi et al. | 250/341 |
| 5,190,039 | 3/1993 | Takeuchi et al. | 128/633 |
| 5,198,977 | 3/1993 | Salb | 128/633 |
| 5,253,646 | 10/1993 | Delpy et al. | 128/633 |

FOREIGN PATENT DOCUMENTS 280986 9/1988 European Pat. Off. .
329115 8/1989 European Pat. Off. .

*Primary Examiner*—Krista M. Pfaffle
*Attorney, Agent, or Firm*—Antonelli, Terry, Stout & Kraus

[57] ABSTRACT

An X-ray tomography scanner and an optical tomography scanner are combined to obtain an optical image indicting metabolism in the body. Optical projection data indicating light pulse transmissions in the body are compensated by using a light scattering coefficient distribution determined by an X-ray tomogram image discriminated into individual internal organs or tissues. The compensated projection are back-projected.

34 Claims, 6 Drawing Sheets

METHOD AND APPARATUS FOR OBTAINING AN IMAGE INDICATING METABOLISM IN A BODY

This is a continuation of application Ser. No. 07/783,216, filed Oct. 28, 1991, now abandoned.

BACKGROUND OF THE INVENTION

The present invention relates to imaging apparatus for diagnosis use to noninvasively measure a quantitative distribution representative of biological function or metabolism in living body and to display the distribution.

Imaging systems for diagnosis use can be grouped into two types, morphological imaging systems and functional quantity imaging systems. With systems of the former type, we can observe the shape of internal organs or tissues. To supply more clinical informations, several kind systems of the later type are now developed. One example is magnetic resonance spectrum (MRS)-imaging system. It was known that some information on metabolic process in tissue can be obtain by measuring chemical shift of resonant frequency of $P^{31}$. Accordingly, many efforts have been made for developing a clinical use MRS imaging system by adapting position mapping methods to the spectroscopic technique of an NMR spectrum analyzer. However, the system has not reached a practical level, because $p^{31}$ resonant signals from a living body are very weak, and the measurement time becomes very long to obtain informations for spectroscopic analysis and position mapping.

Another example of imaging systems for obtaining a spatial distribution representative of a biological function in body is suggested in U.S. Pat. No. 4,281,645. According to that, in vivo monitoring of oxidative metabolism in an internal organ can be practiced through measurement of hemoglobin oxygenation with detection of near infrar red light transillumination.

In such a in vivo optical monitoring system, is a difficult to obtain a practical level of spacial resolution, because a light beam on a living body is heavily scattered at respective regions or organs in the body. The applicant of the present application proposed a multiwavelength method for reducing the adverse effect of the light scattering in body, with U.S. patent application Ser. No. 07/479,171, now U.S. Pat. No. 5,148,022, filed Feb. 13, 1990.

SUMMARY OF THE INVENTION

To improve the poor resolution of functional distribution imaging systems, it would be useful to prepare a functional distribution imaging system and a morphological imaging system and to compare the picture images from both. However, the resolution of images obtained from prior optical imaging systems for metabolism monitor are too poor to recognize the position correspondence with a morphological image. Further, metabolism distribution data analyzed with prior optical systems is not accurate, because of the adverse effect of light scattering in a body cannot be removed.

A data processing method for obtaining a functional distribution is an iteration method. This method can be applied to oxidative metabolism imaging system. In such a system, light absorption coefficients of respective local areas and light scattering coefficients of respective local areas are defined as variables. Measured light distribution is affected by both attenuation and scattering, and both effects should be accurately analyzed to obtain the oxidative metabolism distribution. When the iteration method is applied for analyzing the both, the data processing time becomes very long, because there are many variables.

One object of the present invention is to provide a system which can obtain an accurate functional distribution.

Another object of the present invention is to reduce data processing time for obtaining an accurate functional distribution.

Still another object of the present invention is to improve spacial resolution of functional distribution imaging systems.

According to the present invention, a morphological imaging means and a functional distribution imaging means are combined together with a common field of view so that measurement with both can be practiced simultaneously or without moving the object to be imaged. In a process for analyzing data from the functional distribution imaging means, the values of at least one variable for respective pixels are determined on the basis of a morphological image obtained with the morphological imaging means.

According to a representative embodiment of the present invention, an X-ray computer tomograph scanner is combined with an optical monitoring system which individually detects lights passing through an object for respective ones of a plurality of light irradiation spots and a plurality of light pickup spots, both are arranged on a surface of the body to be inspected. The section image obtained with the X-ray tomograph scanner is discriminated into regions of individual internal organs or tissues. Each of detected optical data is affected with light scattering coefficient distribution and light absorption coefficient distribution, at each light passing area defined by the positions of the light irradiation spot and light pickup spot. Both of the coefficients are defined as variables in an algorithm calculating the light absorption coefficient distribution. Values or variable ranges of light scattering coefficients of respective pixels are determined on the basis of the discriminated X-ray tomogram image. Through the determination of values or variable ranges, calculation time becomes short and an accurate light absorption coefficient distribution can be obtained.

DESCRIPTION OF THE PREFERRED EMBODIMENTS

Figure 1:
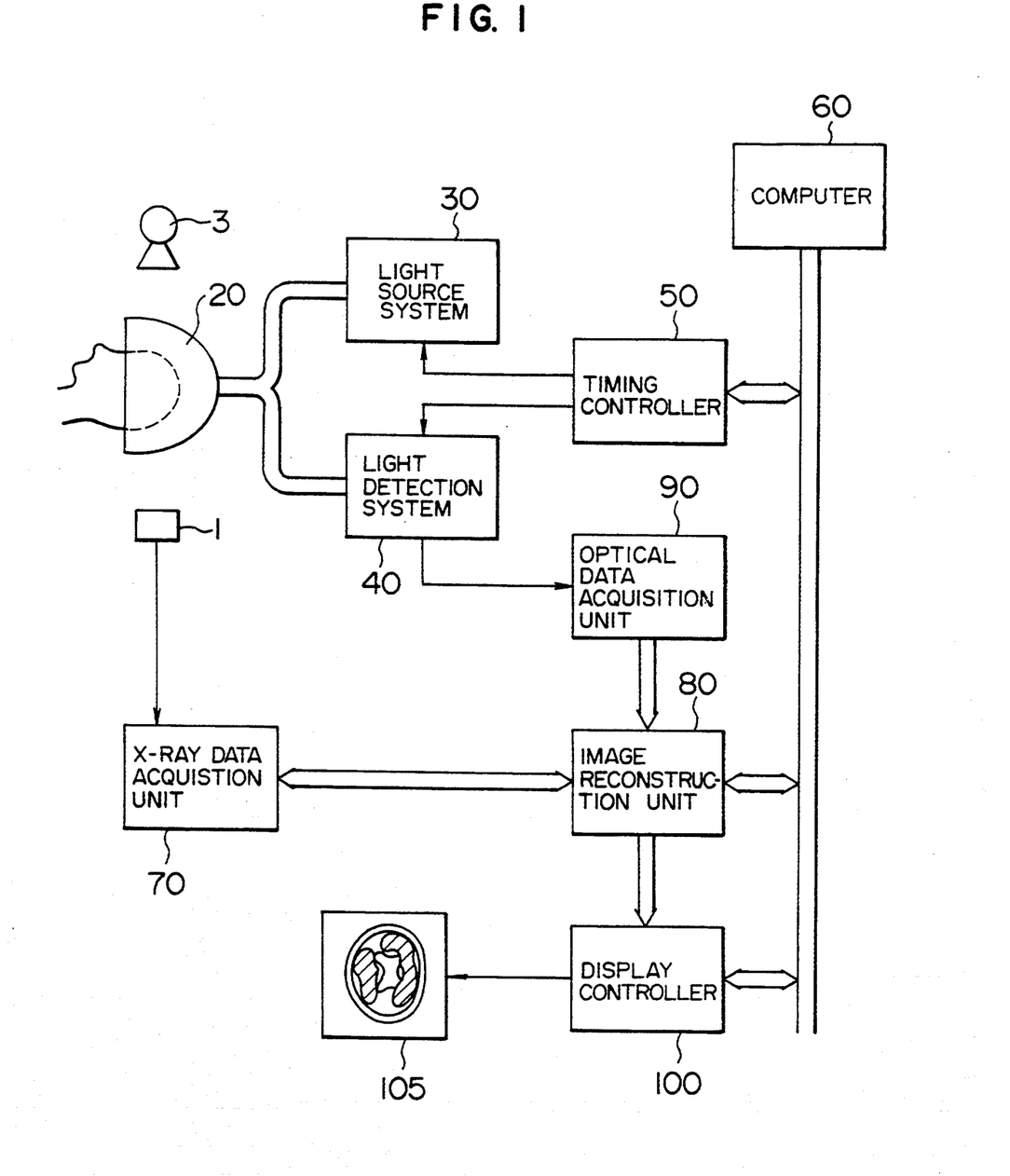
FIG. 1 is a block diagram of an embodiment of the present invention.

FIG. 1 shows the whole structure of an embodiment of the invention. The embodiment includes a morphological data measuring part for obtaining data on morphological image of internal organs or tissues of the body to be inspected, and a functional distribution measuring part for obtaining data on a distribution representative of biological function in the regions of the body. An image reconstructing unit 80 and a display controller 100 are provided commonly to the both parts. The morphological data measuring part employs a measuring principle of X-ray computer tomography scanner (X-ray CT scanner). The X-ray CT scanner includes an X-ray source 3 and an X-ray detector array 1, both mounted on a rotating gantry not shown in FIG. 1. X-ray projection data for respective rotating angles of the gantry is provided to and stored in a X-ray data acquisition unit 70. The functional distribution measuring part employs a measuring principle of optical imaging system which obtains a distribution of a metabolic substance in living body with a spectrophotometric transillumination method (optical CT scanner). The functional distribution measuring part includes an optical couple cap 20 applied to the body to be inspected, a light source system 30, a light detection system 40, a timing controller 50 for controlling the systems 30 and 40, and an optical data acquisition unit 90 for storing measured optical data. Data stored in the both data acquisition units 70 and 90 are subjected to an image reconstructing operation practiced in the image reconstruction unit 80. Image data are applied to the image controller 100, and picture images are displayed on display unit 105. All of the blocks are controlled by a computer 60.

Among the structure, the morphological data measuring part can be displaced by other measuring systems which can obtain image data on an internal section of human body, for example, magnetic resonance imaging (MRI) system. Further, the principle of the embodiment can be applied not only to the above mentioned optical CT scanner, but also magnetic resonance spectroscopic imaging system (MRS imaging system), biomagnetic (neuromagnetic) imaging system or other systems in which biological function in living body, such as circulation or metabolism can be measured and spacially analyzed.

Figure 2:
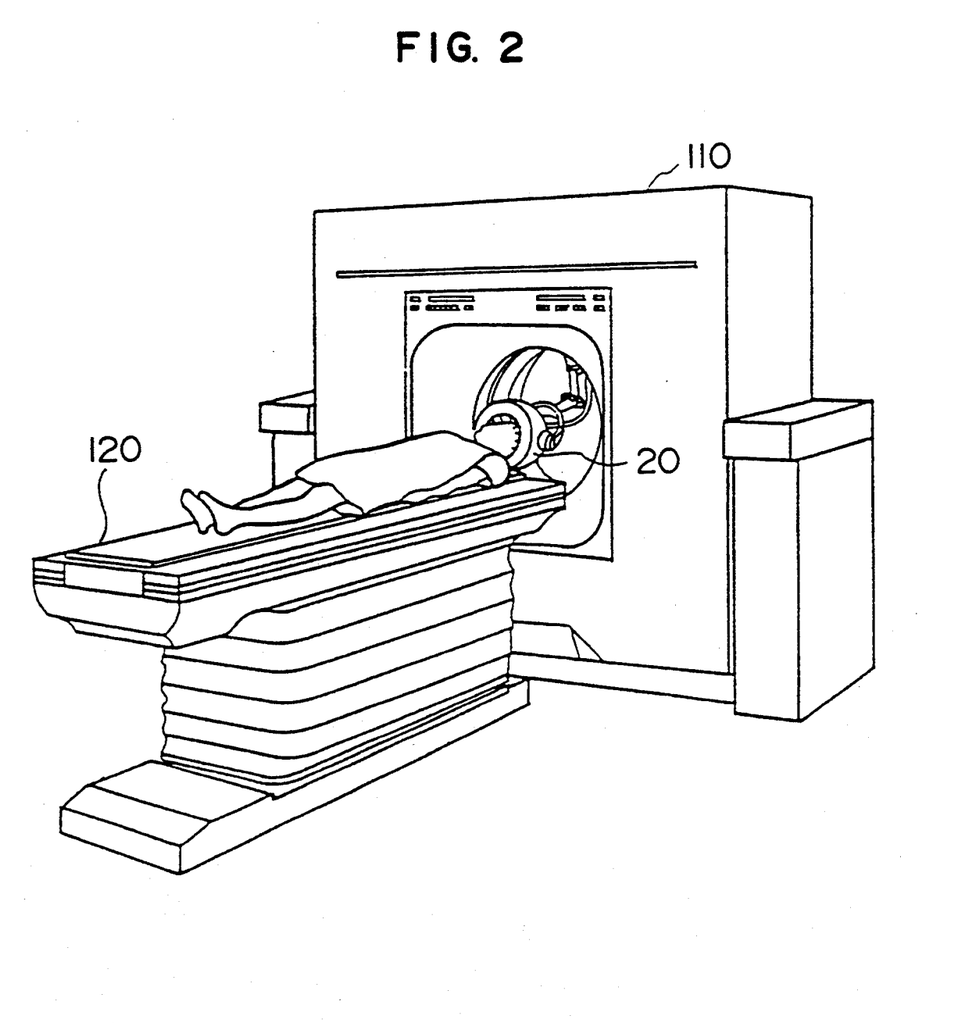
FIG. 2 is an external view of the embodiment.

FIG. 2 shows an external view of the embodiment, which is for monitoring a human head. The optical coupler cap 20 is arranged in a center hole of the main frame 110 of the system. Other blocks shown in FIG. 1 are housed in the main frame 110. The head of a patient lying on a bed 120 is inserted in the center hole of the main frame 110, and the optical coupler cap 20 is settled to the head.

Figure 3:
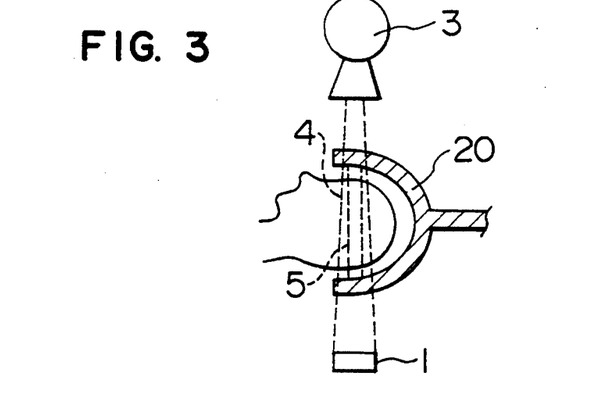
FIG. 3 is a sectional View of a main part of the embodiment showing field of view of two imaging systems in the embodiment.

FIG. 3 shows measurement area or field of view of each of the morphological data measuring part and the functional distribution measuring part. The field of view 4 of the morphological data measuring part is determined by the X-ray detection area of X-ray detector array 1 confronting to the X-ray source 3. The optical coupler cap 20 is disposed across the field of view 4. The field of view 5 of the functional distribution measuring part is restricted within the field view 4 of the morphological data measuring part. Thus, the field of view 4 of the morphological data measuring device covers a section of the optical coupler cap 20 and the field of view 5 of the functional distribution measuring device.

Figure 4A:
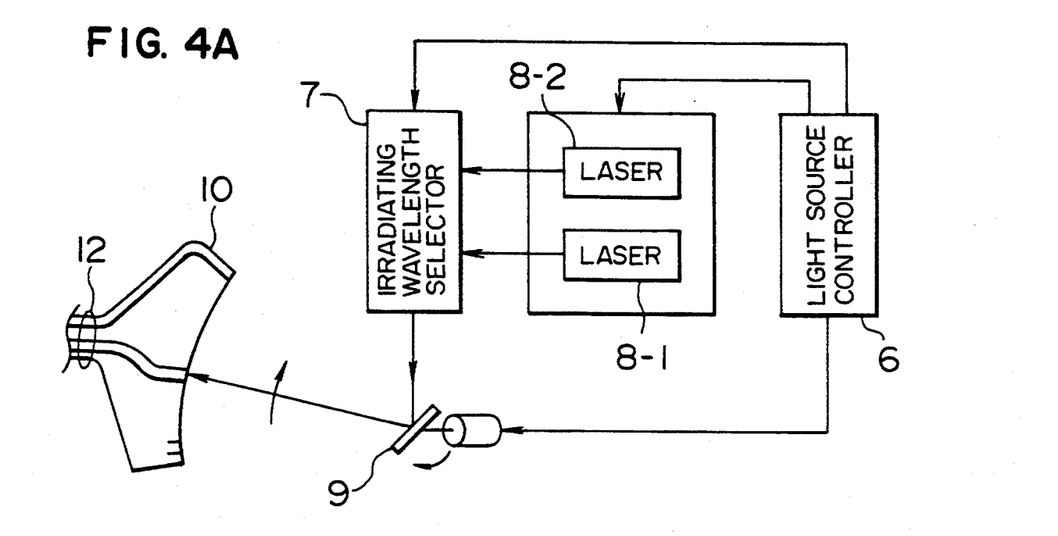
FIGS. 4A and 4B are a block diagram and a sectional view of other parts of the embodiments.

FIG. 4A shows the structure of the light source system 30. The light source system includes two LASER units 8-1 and 8-2 which radiate light pulses of respective wavelengths with pulse width shorter than 100 pico second. An irradiation wavelength selector 7 is controlled by light source control 6 to select one of laser lights from the LASER units 8-1 and 8-2. The selected light pulse is lead to rotating mirror 9, and directed to one of optical fibers 12 arrayed in a light distributor 10 in accordance with the angle of the rotating mirror 9. The rotating mirror is driven by a stepping motor controlled by control pulses from the light source controller 6. Thus, light pulses generated at LASER unit 8-1 and 8-2 are sequentially distributed to each of optical fibers 12.

Figure 4B:
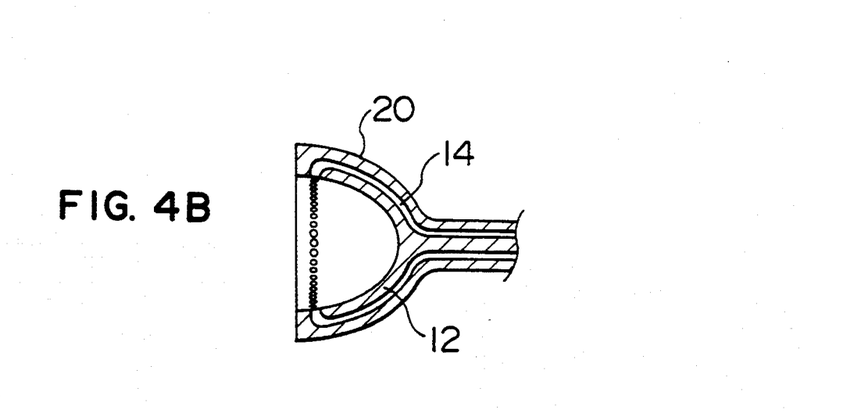

The optical fibers 12 for light irradiation are lead to the optical coupler cap 20, and the ends of respective fibers are aligned along a circular line on the inside surface of the cap 20, as shown in FIG. 4B. Optical fibers 14 for light detection are also aligned along the circular line, and they are lead to light detection system 40. The light radiated from one of optical fiber 12 irradiates the human head in the cap. The light is absorbed and scattered at respective regions or tissues of the head and comes out from the surface of the head. The transmitted lights are picked up at plural positions, and respectively lead to light detection system 40 through the optical fibers 14.

In this embodiment, two wavelengths are alternatively used. One of them is selected to an absorption peak of deoxyhemoglobin (760 nm) and the other is selected to an oxyhemoglobin-deoxyhemoglobin isosbestic point (805 nm). Alternatively, a method of four wavelengths detection can be employed, in which the above mentioned two-wavelengths and wavelengths slightly shifted from the respective ones are used. The four wavelengths detection method is disclosed in U.S. patent application Ser. No. 07/479,171, filed Feb. 13, 1990.

Figure 5:
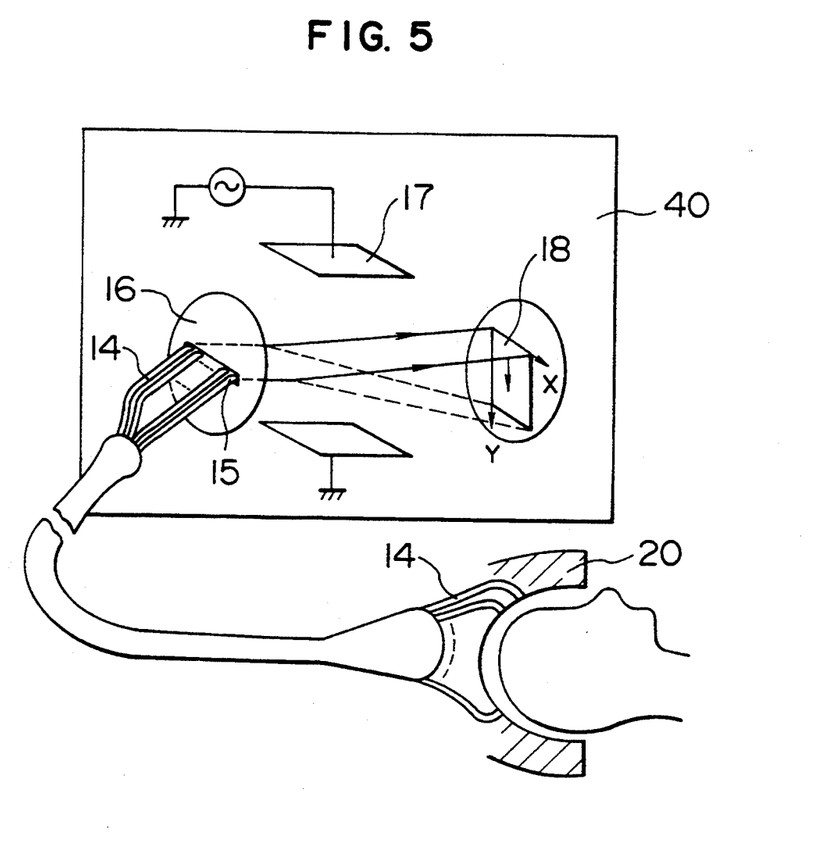
FIG. 5 is an illustrate showing a light detection system of the embodiment.
Figure 6A:
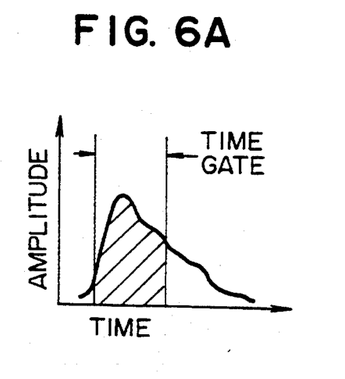
FIGS. 6A and 6B are graphical indication of wave forms detected with the light detection system.
Figure 6B:
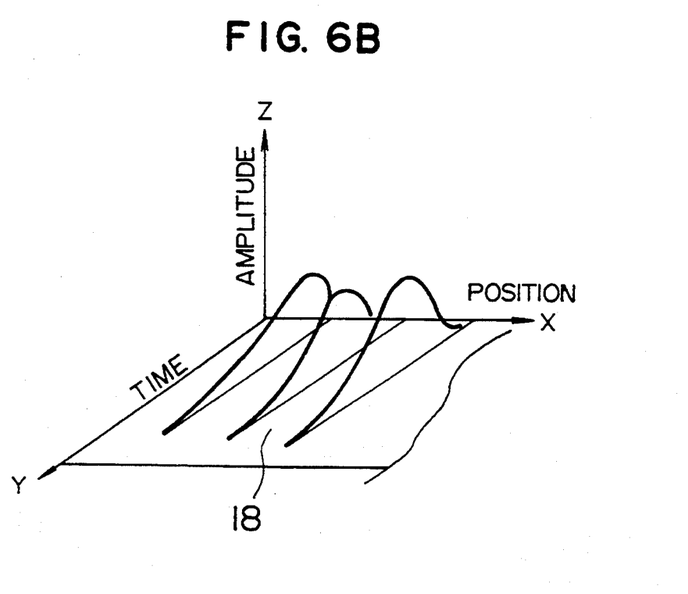

FIG. 5 shows structure of light detection system 40. The light detection system 40 is capable of detecting and recoding time-base variation of light quantity (light time spectrum). Lights respectively transmitted through the optical fibers irradiate respective spots 15 on an optical cathod 16 of a streak camera. Electron beams are generated corresponding to the light irradiation, and the beams fly to an anode 18 coated with a fluorescent material. A high frequency deflecting field is generated with deflecting electrode 17, thereby, the beams are swept along y-direction. Thus, time-base variations of light quantities on respective spots are spreaded on the anode 18 and fluorescent line images appears as shown in FIG. 6B. The line images are picked up with a TV camera (not shown) and recorded in a memory, which is included in the light data acquisition unit 90 shown in FIG. 1. Of each of the recoded data, only the data corresponding to a hatching portion in FIG. 6A are selected and integrated for realizing a time gate eliminating stray light.

Figure 7:
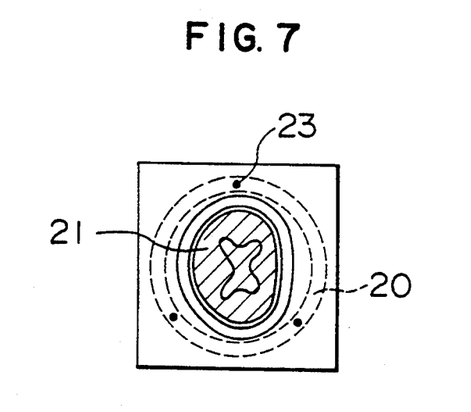
FIG. 7 is a picture image obtained with an X-ray CT scanner in the embodiment.

According to a measurement sequence of the embodiment, a morphological data measurement using X-ray is performed first. The measurement is performed with the optical coupler cap 20 applied to the head of a patient. The cap 20 is made of X-ray permeable materials, such as aluminum and synthetic resin. At least three rod members made of a high X-ray absorption material are buried in the shell of the cap 20. Thereby, a tomogram image 21 of the human head and three position markers 23 appear on an X-ray tomogram image reconstructed in the image reconstruction unit 80 and displayed on a screen of the display unit 105, as shown in FIG. 7. The markers 23 indicate the position of the optical coupler cap 20.

Figure 8A:
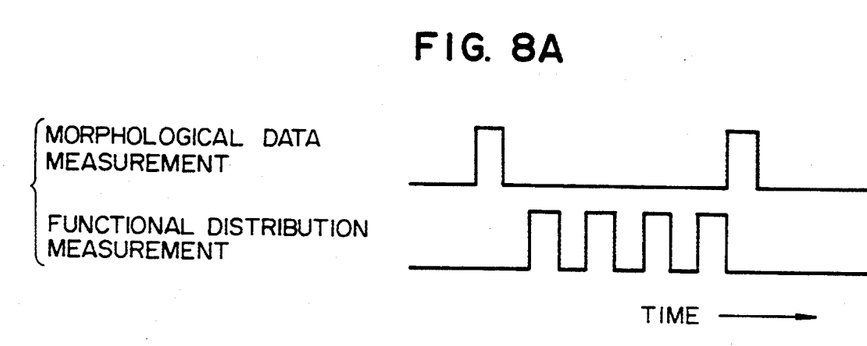
FIG. 8A and FIG. 8B are time charts showing the measurement sequence in the embodiment.
Figure 8B:
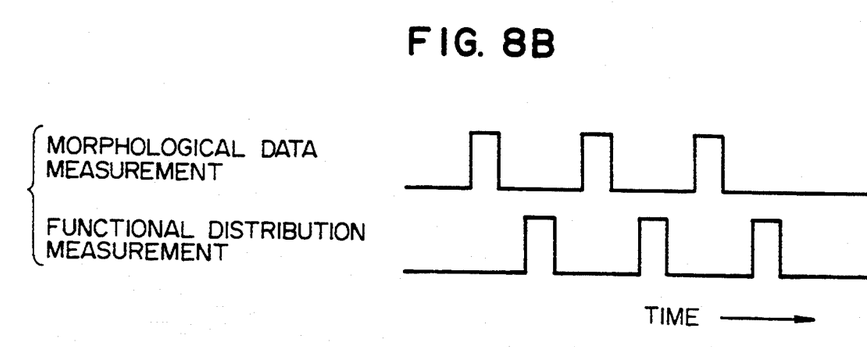

After the measurement using X-ray, a functional distribution measurement using light pulses is performed. To avoid a condition change, it is ideal to practice both measurements at the same time. However, there is no problem associated with practicing both measurements sequentially, because the condition change is negligible. The functional distribution measurement is generally repeated several times to obtain information concerning time-base change of oxidative metabolism. In such a case, the morphological data measurement may be performed again after the repetition of the functional distribution measurement, as indicated in FIG. 8A. When the interval of the repetition is rather long, it is preferable to practice both measurements alternately, as indicated in FIG. 8B.

To obtain one image indicating distribution of light absorption coefficient in a section, transillumination characteristics of the object in many directions should be measured. Accordingly, the selection of optical fibers 12, namely the selection of irradiation spot on the head, is sequentially shifted and the detection of transmitted light pulse at a plurality of light pickup spots is repeated. Through the repetition, data consisting of Ns.Nd numerical values are acquired and stored in the light data acquisition unit 40, where Ns is number of light irradiation spots, and Nd is number of light pickup spots per one time light pulse-transmission.

The algorithm used for image reconstruction in the embodiment is based on a back-projection method, which is disclosed in "Image Reconstruction from Projection" by G. T. Herman, 1979. Further, image reconstruction operation of the embodiment utilizes information from previously obtained morphological image.

At first, the whole imaging area of the previously obtained X-ray tomogram image shown in FIG. 7 is divided into elements of N.M matrix. The elements are corresponding to pixels of the light absorption coefficient distribution image to be derived. Then, positions of all of the light irradiation spots and light pickup spots are calculated using the positions of the markers 23 shown in FIG. 7. Then, an operation of region discrimination is practiced on the X-ray tomogram image to discriminate the image into individual regions of internal tissues such as bone, white matter of brain and gray matter of brain. Automatic region discrimination methods used in three-dimensional indication of internal organs can be employed. A simple method is to discriminate using CT value of each pixel. For example, pixels indicating CT values higher than 1200 are concluded as bone, pixels having CT values between 1100 and 1200 are white matter of brain, and pixels inside of the bone having CT values lower than 1100 are gray matter of brain. Thus, a discriminated head image is derived and stored in a memory.

Figure 9A:
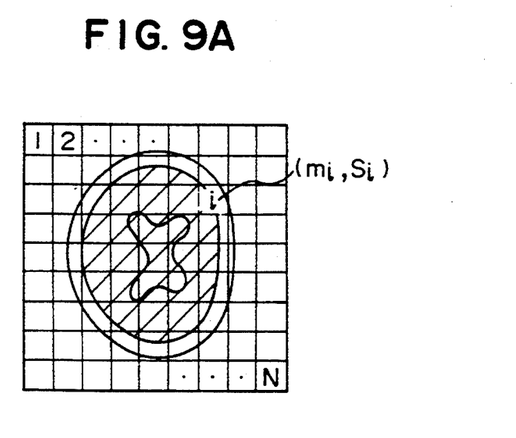
FIG. 9A–FIG. 9E are conceptional diagrams showing data processing operation in the embodiment.

Then, optical variables for each pixel are defined as $s_i$ and $m_i$, as shown in FIG. 9A, where $s_i$ is light scattering coefficient, $m_i$ is light absorption coefficient and i is pixel number. Values of some of those optical variables can be assumed from the discriminated X-ray head image and wavelength of light pulse used in optical measurement. Therefore, constant values are determined for these optical variables. For example, when the wavelength is within 600–700 nm, the value $m_i$ for pixels of bone region can be determined as $m_i=0$. The value $s_i$ for bone region can be determined from the age of the patient. The value $s_i$ for other regions can be determined from respective standard values, which are known by in vitro tests for respective tissues.

Figure 9B:
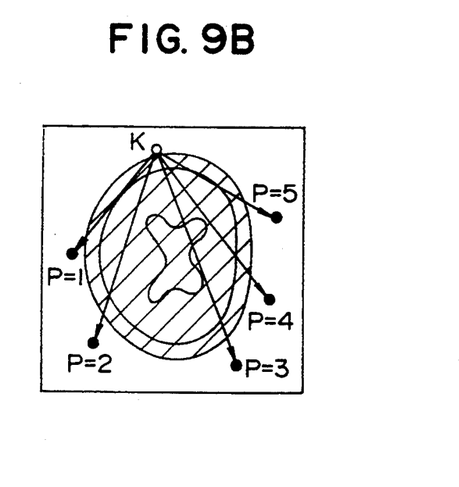

Through the operation of the value determination, $m_i$ for pixels of brain remain as variables in image reconstructing operation. The operation uses light measurement data $A(k,p)$ and $A_0(k,p)$, where $A(k,p)$ is a time-gated integrated value of detected light quantity described before, $A_0(k,p)$ is integrated value of light quantity detected without insertion of patient's head, k is position number of light irradiation spot, k=1, 2, - - -, and p is position number of light pickup spot, p=1, 2, 3, - - -, for each value of k. FIG. 9B shows positions of the light pickup spots for one of the light irradiation spot k.

Light attenuation $X(k,p)$ of the head for each pair of a light irradiation spot and a light pickup spot is calculated from detected data as follows;

$$X(k,p) = -\log\{A(k,p)/A_0(k,p)\} \quad (1)$$

Figure 9C:
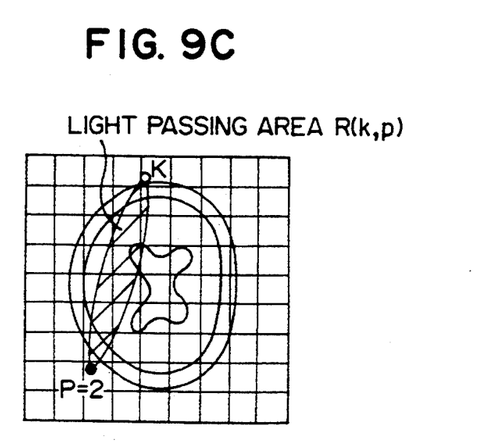

Then, light passing area $R(k,p)$ is defined for each pair a light irradiation spot and a light pickup spot, as shown in FIG. 9C. The shape of the area should be determined in accordance with the width of before mentioned time gate for eliminating stray light. The light attenuation $X(k,p)$ should be given as follows;

$$X(k,p) = \Sigma(m_i + s_i), i \epsilon R \quad (2)$$

where, R denotes a set of pixel number of all of pixels lies in area R(k,p).

Since the values of $s_i$, $i \epsilon R$, are determined from the discriminated X-ray tomogram image, a value $Y(k,p)$ representative of light attenuation only due to light absorption in head can be calculated as follows;

$$Y(k,p) = X(k,p) - \Sigma(s_i), i \epsilon R. \quad (3)$$

Figure 9D:
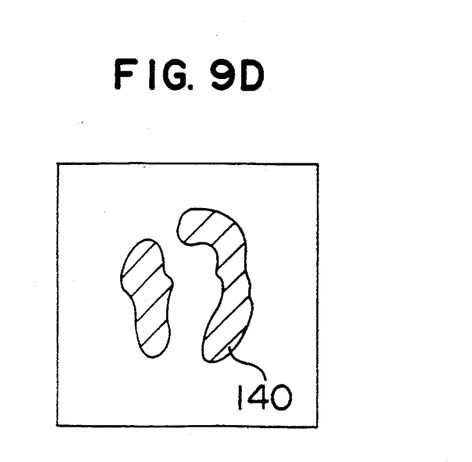
Figure 9E:
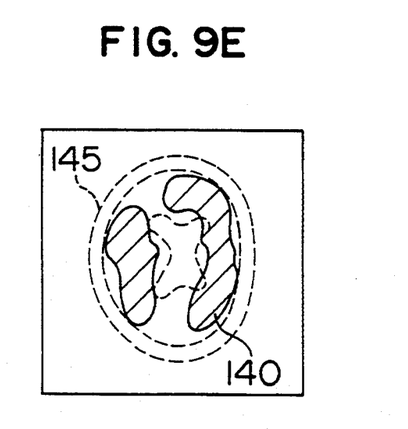

Further, since mfor bone is determined to zero, the calculated values of $Y(k,p)$, (p=1, 2, 3, 4 - - - ) indicate a projection of light absorption coefficient $m_i$ in brain. Such a projection is calculated for respective positions of light irradiation spot, and a data set for reconstructing a light absorption distribution in brain is obtained. Then, an image of the light absorption distribution 140 shown in FIG. 9D is reconstructed through back-projection method. By a proper selection of light wavelengths disclosed in U.S. Pat. No. 4,281,645, a distribution of hemoglobin oxygenation is obtained. As shown in FIG. 9E, the light absorption distribution 140 and X-ray tomogram image 145 are displayed on a single screen with individual colors.

The algoithm of the embodiment can be summarized as follows:

i) Discriminating a morphological image into individual regions of internal organs or tissues.

ii) Obtaining a plurality of data $A_p$ (p=1, 2, - - - ) through functional distribution measurement. The respective data Ap are effected with distributions of several physical quantities (a, b, c) in respective limited region $R_p$. The data can be indicated by a function having variables $a_i$, $b_i$, $c_i$, as follows:

$$A_p = ( - - - a_i - - - , - - - b i - - - , - - - c_i - - - ) i \epsilon r_p \quad (4)$$

iii) Determining the values of variables $b_i$ and $c_i$ by an assumption according to respective standard values of physical quantity b and c for each of internal organs or tissues. Then, the equation (4) becomes as follows:

$$A_p = f'(---a_i---), i \epsilon R_p \qquad (5)$$

iv) Calculating values $a_i$ in a determined region from the equation (5) and detected values $A_p$ (p=1, 2, ---), to obtain an image of distribution of the variable $a_i$, which indicating a biological function.

According to the embodiments, the values of some variables are determined to constant values. It is also effective to determine the variable ranges of some variables using a region discriminated morphological image. When more than a particular number of measurement values $A_p$ in equation (4) are given, the variables $a_i$, $b_i$ and $c_i$ can be obtained by iteration method. However, the operation of iteration method takes a very long time, if none of the variable ranges of the variables $a_i$, $b_i$ and $c_i$ are known. According to our invention, the variable ranges of some of the variables are limited by using the region discriminated morphological image. Thereby, the solutions of reverse problem can be obtained in shorter time.

What is claim is:

1. An apparatus for obtaining an image indicating metabolism in a body, comprising:
   morphological imaging means for obtaining a morphological image of a section of a body,
   means for discriminating the morphological image into respective regions of internal organs or tissues,
   functional distribution detecting means for detecting a plurality of detection data, respectively affected with distributions of first and second physical quantities of the body at the respective regions of the discriminated morphological image, and
   image reconstruction means for reconstructing an image indicating the distribution of said first physical quantity in said section of the body, by using the plurality of detection data, and by determining values of said second physical quantity based on the discriminated morphological image at respective pixels of the discriminated morphological image.

2. An apparatus according to claim 1, wherein said functional distribution detecting means detects light pulse transmissions at a wavelength for respective ones of a plurality of light irradiation spots on said body and a plurality of light pickup spots on said body.

3. An apparatus according to claim 1, wherein said morphological imaging means is an X-ray computer tomography scanner obtaining an X-ray tomogram image of the section of the body.

4. An apparatus according to claim 3, wherein said discriminating means discriminate the morphological image into individual regions according to CT values of respective pixels of the X-ray tomogram image.

5. An apparatus according to claim 1, further comprising means for displaying said discriminated morphological image in conjunction with said image indicating the distribution of the first physical quantity.

6. An apparatus according to claim 5, wherein the means for displaying includes a single display screen, and wherein said discriminated morphological image in conjunction with said image indicating the distribution of the first physical quantity are displayed on said single display screen.

7. An apparatus according to claim 1, further comprising control means for controlling said morphological imaging means and said functional distribution detecting means so as to be operated simultaneously.

8. An apparatus according to claim 1, further comprising control means for controlling said morphological imaging means and said functional distribution detecting means so as to be operated alternately.

9. An apparatus for obtaining an image indicating metabolism in a body comprising:
   an x-ray tomography scanner for obtaining an x-ray tomogram image of a section of the body,
   means for discriminating the x-ray tomogram image into individual regions of internal organs or tissues,
   light source means for radiating the body with light pulse transmissions,
   an optical tomography scanner for detecting the light pulse transmissions at a wavelength for respective ones of a plurality of light irradiation spots and a plurality of light pickup spots on said body, and
   optical tomography image reconstructing means for reconstructing a distribution of a light absorption coefficient at said wavelength in said section of the body, including means for calculating a plurality of projections of the light absorption coefficient from the light pulse transmissions detected by the optical tomography scanner and from values of a light scattering coefficient determined on a respective pixel of said discriminated x-ray tomogram imaged and means for calculating back-projection data from the projections of the light absorption coefficient.

10. An apparatus according to claim 9, wherein said optical tomography scanner includes an optical coupler applied to the body and positioned in a field of view of said X-ray tomography scanner.

11. An apparatus according to claim 10, said optical coupler having a shell made of X-ray permeable materials and rods made of a high X-ray absorption material and buried in the shell.

12. An apparatus according to claim 9, including means for operating said optical tomography scanner and said X-ray tomography scanner simultaneously.

13. An apparatus according to claim 9, including means for operating said optical tomography scanner and said X-ray tomography scanner alternately.

14. An apparatus for obtaining an image indicating metabolism in a body, comprising:
   morphological imaging means for obtaining a morphological image of the body,
   means for discriminating the morphological image into respective regions of internal organs or tissues,
   functional distribution detecting means for detecting a plurality of detection data, respectively affected with distributions of first and second physical quantities of the body at the respective regions of the discriminated morphological image, the first physical quantity being indicative of metabolism of the body, and
   image reconstruction means for reconstructing an image indicating the distribution of said first physical quantity in the body, by determining variable ranges of said second physical quantity at respective pixels from the discriminated morphological image, including means for calculating the first and second physical quantities by an iteration method using the variable ranges and the plurality of detection data.

15. An apparatus according to claim 14, further comprising control means for controlling said morphological imaging means and said functional distribution detecting means so as to be operated simultaneously.

16. An apparatus according to claim 14, further comprising control means for controlling said morphological imaging means and said functional distribution detecting means so as to be operated alternately.

17. A method for obtaining an image indicating metabolism in a body, comprising the steps of:
   (a) obtaining a morphological image of a section of the body;
   (b) discriminating the morphological image into respective regions of internal organs or tissues;
   (c) detecting a plurality of functional detection data, respectively affected with distributions of first and second physical quantities of the body at the respective regions of the discriminated morphological image; and
   (d) reconstructing an image indicating the distribution of said first physical quantity in said section of the body, by using the plurality of functional detection data, and by determining values of said second physical quantity based on respective pixels of the discriminated morphological image.

18. A method according to claim 17, wherein said functional detection data are detected optically.

19. A method according to claim 17, wherein said morphological image is an X-ray tomogram image.

20. A method according to claim 19, wherein the morphological image is discriminated into the respective regions according to CT values of respective pixels of the X-ray tomogram image.

21. A method according to claim 17, further comprising the step of:
   (e) displaying said discriminated morphological image in conjunction with said image indicating the distribution of the first physical quantity.

22. A method according to claim 21, wherein said morphological image in conjunction with said image indicating the distribution of the first physical quantity are displayed on a single display screen.

23. A method according to claim 17, wherein said functional detection data are detected by an optical tomography scanner, and said morphological image is an X-ray tomogram image obtained by an X-ray tomography scanner.

24. A method according to claim 23, wherein said optical tomography scanner and said X-ray tomography scanner are operated simultaneously.

25. A method according to claim 23, wherein said optical tomography scanner and said X-ray tomography scanner are operated alternately.

26. A method according to claim 17, wherein said steps of (a) and (c) are effected simultaneously.

27. A method according to claim 17, wherein said steps of (a) and (c) are effected alternately.

28. A method for obtaining an image indicating metabolism in a body, comprising the steps of:
   (a) obtaining a morphological image of a section of the body;
   (b) discriminating the morphological image into respective regions of internal organs or tissues;
   (c) obtaining a plurality of functional distribution data for said section of the body, each of the plurality of data relating to a first physical quantity and a second physical quantity of the body;
   (d) determining the second quantity, for the plurality of functional distribution data, in accordance with the discriminated morphological image;
   (e) calculating the first physical quantity, in accordance with the determined second physical quantity; and
   (f) displaying an image of at least one of the functional distribution data, the calculated first physical quantity, and the determined second physical quantity.

29. A method according to claim 28, wherein said steps of (a) and (c) are effected simultaneously.

30. A method according to claim 28, wherein said steps of (a) and (c) are effected alternately.

31. A method for obtaining an image indicating a functional distribution in a body, comprising the steps of:
   (a) obtaining a morphological image of a section of the body;
   (b) discriminating the morphological image into respective regions of internal organs or tissues;
   (c) detecting at least one physical quantity correlating to said functional distribution for said section of the body;
   (d) obtaining a plurality of physical distribution data for said section of the body from the detected at least one physical quantity;
   (e) changing the plurality of physical distribution data into a functional distribution for said section of the body; and
   (f) displaying an image of the functional distribution in conjunction with the morphological image.

32. A method in accordance with claim 31, wherein a variable range of the at least one physical quantity in determined in accordance with the morphological image.

33. A method according to claim 31, wherein said steps of (a) and (c) are effected simultaneously.

34. A method according to claim 31, wherein said steps of (a) and (c) are effected alternately.

* * * * *